United States Patent [19]

Doleschel et al.

[11] Patent Number: 4,880,913
[45] Date of Patent: Nov. 14, 1989

[54] PROCESS FOR THE PREPARATION OF AN IMMUNOGLOBULIN WHICH CAN BE ADMINISTERED INTRAVENOUSLY AND IS STABLE IN LIQUID FORM

[75] Inventors: Walter Doleschel; Walter N. Doleschel; Werner Conrad, all of Vienna, Austria

[73] Assignee: Schwab & Co. Ges.m.b.H., Vienna, Austria

[21] Appl. No.: 127,914

[22] Filed: Dec. 2, 1987

[30] Foreign Application Priority Data

Dec. 2, 1986 [DE] Fed. Rep. of Germany ....... 3641115

[51] Int. Cl.$^4$ .................... A61K 39/395; C07K 15/06; C07K 15/14
[52] U.S. Cl. .................................. 530/387; 424/85.8; 424/101
[58] Field of Search .................. 530/387; 424/85, 101

[56] References Cited

U.S. PATENT DOCUMENTS

| | | | |
|---|---|---|---|
| 3,429,867 | 2/1969 | Bozicevich | 530/387 X |
| 3,607,857 | 9/1971 | Nelson | 530/387 |
| 3,664,994 | 5/1972 | Perper | 530/387 |
| 3,869,436 | 3/1975 | Falksveden | 530/387 X |
| 4,124,576 | 11/1978 | Coval | 260/112 B |
| 4,136,094 | 1/1979 | Condie | 424/101 X |
| 4,165,370 | 8/1979 | Coval | 424/85 |
| 4,276,283 | 6/1981 | Eibl et al. | 424/85 |
| 4,318,902 | 3/1982 | Stephan | 530/387 X |
| 4,351,710 | 9/1982 | Jain | 204/180 P |
| 4,371,520 | 2/1983 | Llemura et al. | 530/387 X |
| 4,379,086 | 4/1983 | Kimura et al. | 2160/112 B |
| 4,434,093 | 2/1984 | Zolton et al. | 530/387 |
| 4,482,483 | 11/1984 | Curry et al. | 424/85 X |
| 4,762,714 | 8/1988 | Mitra et al. | 424/101 |

FOREIGN PATENT DOCUMENTS

| | | |
|---|---|---|
| 1201063 | 2/1986 | Canada . |
| 0085747 | 8/1983 | European Pat. Off. .............. 424/88 |
| 85747 | 8/1983 | European Pat. Off. . |
| 0123029 | 10/1984 | European Pat. Off. . |
| 196761 | 10/1986 | European Pat. Off. . |
| 3430320 | 3/1985 | Fed. Rep. of Germany . |
| 2301266 | 9/1976 | France . |
| WO84/00891 | 3/1984 | PCT Int'l Appl. . |
| 1006258 | 9/1965 | United Kingdom . |

OTHER PUBLICATIONS

Skoog, Experientia 36 (1980), pp. 1157–1158 Chemical Abstracts 94:127193m (1981).

*Primary Examiner*—Howard E. Schain
*Attorney, Agent, or Firm*—Wenderoth, Lind & Ponack

[57] ABSTRACT

The invention relates to a process for the preparation of an immunoglobulin which has no side effects, is stable on storage in liquid form and can be administered intravenously and which has a monomer content above 97%, in which euglobulins and other impurities are removed from a previously purified immunoglobulin solution by precipitation and adsorption on an ion exchanger, the immunoglobulin is stabilized by acid and heat treatment and is further purified by another ion exchanger treatment, and aggregated proteins are removed by precipitation with low molecular weight PEG. The solution is converted by ultra- and diafiltration into a form which can be used.

8 Claims, No Drawings

PROCESS FOR THE PREPARATION OF AN IMMUNOGLOBULIN WHICH CAN BE ADMINISTERED INTRAVENOUSLY AND IS STABLE IN LIQUID FORM

The present invention relates to an improved process for the preparation of a chemically unmodified immunoglobulin G (IgG) which has not been enzymatically treated and is essentially free of immunoglobulin A (IgA), and which has no side effects, consists of virtually pure IgG and is provided in the form of a clear stable aqueous solution or as a freeze-dried product for intravenous administration.

U.S. Pat. No. 4 165 370 describes a multistage process for the preparation of a gamma-globulin product which is tolerated intravenously. This entails in a stage a) an euglobulin precipitation being carried out at pH 4.8 to 6.5, in a stage b) precipitation out of impurities using polyethylene glycol (PEG) having a molecular weight of 4,000 at a concentration of 4 and 5%, and in stage c) precipitation of the IgG using PEG 4,000 at a concentration of 12%. However, no statements are made in this US-PS 4 165 370 about the purity of the product, in particular about the monomer content. The products obtained by this process have the disadvantage, however, that the PEG which is used as precipitant remains in the product. Furthermore, it is necessary to add for stabilization albumin and a surface-active agent. However, the latter is undesired from the medical standpoint.

EP-PS 123 029 discloses a multistage process for the preparation of an IgG solution which can be administered intravenously and is stable on storage in liquid form, but which is not entirely satisfactory with regard to yield, simplicity of the process and purity of the product, there also being problems with the disposal of the precipitant in an environmentally acceptable manner.

Thus, the object was to develop a simpler process, providing good yields, for the preparation of a virtually pure immunoglobulin which can be administered intravenously and is stable on storage in liquid form, or is freeze-dried.

This object is achieved according to the invention by subjecting a previously purified IgG solution to a combination of several successive and mutually harmonized treatment steps. In a first stage, undesired concomitant proteins are removed by an euglobulin precipitation, then follows an acid stabilization and a treatment with an anion exchanger which removes immunoglobulins which do not belong to the IgG class, for example IgA, as well as other impurities and part of the unphysiological IgG aggregates. In another step, IgG aggregates and other high molecular weight concomitant proteins are precipitated using low molecular weight polyethylene glycol (PEG) as precipitant, and the supernatant pure IgG solution is converted by ultra- and diafiltration into a form which is stable on storage and can be injected. The advantage of the low molecular weight PEG over the high molecular weight PEG which is used in the state of the art and has molecular weights between 4,000 and 6,000 consists in that low molecular weight PEG can be completely removed by dialysis, and it has proved particularly advantageous to carry out in one ultrafiltration system the removal of the PEG in combination with the concentration of the protein solution which is necessary after each fractionation.

Accordingly, the present invention relates to an improved process for the preparation of a chemically unmodified, functionally and structurally intact immunoglobulin which has not been enzymatically treated, has no side effects, contains all IgG subclasses, is essentially free of IgA, is stable on storage in liquid form and can be administered intravenously, and which has a monomer content of above 97% and a content of trimers and higher polymers of below 1%, by subjecting a starting fraction which has been prepared by known processes to purification and concentration in several steps, such as dialysis, adsorption and precipitation, which comprises (a) dialysis of an aqueous solution of the starting fraction to remove low molecular weight constituents, lowering the ionic strength at a pH of 6.0–9.0 to below 500 $\mu$S in order to remove euglobulins, where appropriate removal of impurities from the supernatant from the euglobulin precipitation by adsorption once or twice on an anion exchanger in an amount of 5–50 mg/g protein at a pH of 6.0 to 9.0, (b) stabilization of the solution by acid treatment at pH 2.5–4.2, where appropriate heating at 40°–60° C. and pH 3.0–8.0 for 15 to 120 minutes, returning the pH to 7.0–9.0, and removal of the insoluble fractions by centrifugation, (c) removal of IgA and other impurities which are still present by treatment once or twice with an anion exchanger in an amount of 5–50 mg/g protein at pH 6.0–9.0, (d) addition, where appropriate, of the substances present in the final buffer to the solution, precipitation of labile and aggregated IgG molecules by addition of polyethylene glycol having a mean molecular weight of 200–1,000 to a final concentration of 10–25% (w/w) and removal thereof by centrifugation, addition of the substances present in the final buffer to a solution which does not yet contain these substances, removal of the precipitant, adjustment of the solution to the desired protein concentration, and sterilization thereof by filtration.

Suitable as starting material for the process according to the invention are all fractions of a normal or hyperimmune plasma, and all products which can be administered intramuscularly and have an IgG content between 30 and 100% of the total protein. Fractions of this type can be obtained, for example, as fraction II +III or fraction II by Cohn ethanol fractionation. Similar fractions can also be prepared, for example, by ammonium sulfate precipitation, or polyethylene glycol or rivanol fractionation. However, it is also possible to subject to the process according to the invention finished products which are intended for intramuscular administration or which are not stable on storage in liquid form and have been prepared for intravenous administration.

European Patent 123 026 proposes as first purification stage for the precipitation out of the euglobulins the adjustment to a conductivity of less than 300 $\mu$S at a pH of 5.3 to 5.5, followed by addition of BaSO$_4$ to adsorb proteolytic enzymes. It has now been established, surprisingly, that the adsorption on a mineral adsorbent can be omitted if the euglobulin precipitation in stage a) is carried out, after removal by dialysis against distilled water of low molecular weight constituents and any residues which are present of precipitant, such as, for example, ethanol, at a conductivity of below 500 $\mu$S and a pH of 6.0 to 9.0, preferably 6.5 to 7.5. The removal of the euglobulin precipitate can be followed, if a starting material with a relatively low degree of purity has been used, by treatment of the clear solution once or twice with a weak anion exchanger. Suitable for this purpose are all the weak anion exchangers prepared for the treatment of biological substances, such as, for example, DEAE-Sephadex ®, DEAE-sepharose, DEA cellulofine and the like. The use of DEAE-Sephadex ® A 50 in an amount of about 5.0 to 50 mg, preferably 10–30 mg, of ion exchanger (dry weight) per gram of protein at a pH of 6.0 to 9.0, preferably pH 6.5 to 7.5, has proved appropriate for this.

The solution obtained after stage a) is subjected in stage b) to an acid treatment to increase the stability and to reduce the anticomplementary activity. Depending on the duration of this treatment, it can take place at a pH of 2.5 to 4.2, preferably of 2.9 to 3.9, the adjustment of a pH of 3.3 to 3.5 in turn being particularly preferred. In an expedient embodiment it is possible to carry out this treatment in two stages by initially adjusting the pH of the solution with 1N HCL, at 0°–10° C., preferably at 4° C., to about 2.9 to 3.1, and leaving it at this pH for 5 to 10 minutes. A pH of 3.3 to 3.5 is subsequently adjusted by addition of a base, preferably of ammonia, and the clear solution is maintained at 0°–10° C. for 12–72 hours, preferably 12 to 24 hours.

The pH is adjusted to about 7.0 to 9.0, preferably pH 8.0 to 8.5, by further addition of a base, and the mixture is left to stand for 0.5 to 5 hours, preferably 1–3 hours, for the flocculation of aggregates and denatured proteins. It is also possible, where appropriate, before the pH is returned to 7.0 to 9.0, for the solution to be heated at about 40°–60° C. for about 15 minutes to 2 hours at pH 3.0 to 8.0, preferably at 45°–55°C. for half an hour to one hour. In this connection, a heat treatment in the acid range results in a particularly stable product, whereas a heat treatment in the neutral to slightly alkaline range results in higher yields. The removal of the precipitate can then be carried out in a customary manner by filtration, centrifugation or decantation.

If the desired immunoglobulin product is not intended to be in liquid form, the acid and heat treatment is not absolutely necessary.

In a stage (c), the supernatant from stage (b) is treated once or twice with a weak anion exchanger. The use of DEAE-Sephadex ® A 50 in an amount of about 5–50 mg (dry weight) per gram of protein at a pH of 6.0 to 9.0, preferably 10 - 30 mg at pH 7.0 to 7.5, has once again proved appropriate. Adjustment of a neutral to slightly alkaline pH results in an IgG product which is particularly low in IgA.

The removal of dimers and aggregates of IgG and of high molecular weight impurities and labile proteins in step d) is effected by addition of low molecular weight polyethylene glycol (PEG) with a mean molecular weight of 200–1,000, preferred molecular weights being from 600 to 1,000. In this connection, the final concentration of PEG for the precipitation out of the above-mentioned constituents of the IgG solution depends substantially on the molecular weight of the PEG, and ranges from about 10 per cent by weight with PEG 1,000 to about 25 per cent by weight with PEG 200. The pH of the solution during the PEG precipitation should be between about 6.0 and 8.0, preferably between 6.5 and 7.5. The precipitation is advantageously stored at 4° C. overnight before the precipitate is removed by centrifugation.

The substances used in the final buffer are now added to the IgG solution. It is possible to use for this purpose all physiological buffers which are compatible with IgG, such as, for example, phosphate buffer, glycine/sodium chloride and the like. This step can also be carried out before the PEG precipitation. The PEG can be removed by methods customary in biochemistry, such as reprecipitation, dialysis, and ultra- and diafiltration. However, in this connection it is particularly preferred to transfer the clear solution into an ultrafiltration system and there simultaneously to adjust the desired protein concentration and the desired buffer and to remove the PEG from the IgG solution by dia- and ultrafiltration against a 5-fold excess of the final buffer.

Subsequently, the IgG solution, which contains at least 97% monomers, but usually more than 99% monomers, is sterilized by filtration and dispensed into containers.

In a preferred fashion, the finished gammaglobulin product is stored in a liquid form ready for use, this being stable even on prolonged storage. However, if desired, it can also be freeze-dried.

Example 1

25 g of Cohn precipitate II-1,2 with a protein content of 25.6% were mixed with 25 ml of demineralized water, and the suspension was stirred at +4° C. until homogeneous. It was then dialyzed at +4° C. against running demineralized water. After 48 hours, the mixture was diluted with 4 times the amount of demineralized water, and a sodium chloride concentration of 1 mmol/l was set up. The solution was centrifuged, and the precipitate, which contained a high proportion of high molecular weight proteins, was discarded.

The supernatant was mixed with 20 mg of DEAE-Sephadex A 50 (dry weight) per gram of protein, and the mixture was stirred at +4° C. for 2 hours. The ion exchanger was filtered off through a suction funnel, the pH was adjusted back to 7.0, and the treatment with DEAESephadex A 50 was repeated.

The pH of the protein solution was adjusted to 2.9 by addition of 1N HCL and, after stirring for 10 minutes, a pH of 3.3 was adjusted by addition of ammonia solution, and the solution was stored at +4° C. overnight. The pH was increased to 8.25 by further addition of ammonia solution, the solution was stored at +4° C. for 2 hours for the flocculation of aggregates, and the resulting precipitate was removed by centrifugation and discarded.

To remove small residues of labile IgG molecules and proteolytic enzymes, the solution was again stirred with anion exchanger (20 mg/g protein) at +4° C. for 2 hours and then filtered with suction.

In order to ensure a purity content of monomeric immunoglobulin G in the final solution which is greater than 97%, but is greater than 99% as a rule, a precipitation was carried out by addition of PEG 1,000 (as a 50% strength aqueous solution) to a content of 10% (w/w). The precipitation was stored at +4° C. overnight before the precipitate was removed by centrifugation.

The pure IgG solution was then stabilized by addition of glycine (15 g/l) and NaCL (7 g/l), and PEG 1,000 was removed by ultra- or diafiltration through a millipore PTGC 00005 cassette with a molecular weight exclusion limit of 10,000 against five times the amount of glycine/NaCL buffer, there being a simultaneous increase in the protein concentration to 49.89 mg/ml. The solution was then sterilized by filtration and dispensed into containers.

Yield: 98 ml

Anticomplementary activity: 16.9

(The anticomplementary activity was determined by the method of KABAT, E.A. and MAYER, M.M.: Experimental Immunochemistry, 2nd Ed., Charles C. Thomas, p. 135–153, 1961).

|  | % protein | % monomers | % dimers | % polymers | IgA titer |
|---|---|---|---|---|---|
| dissolved precipitate II-1,2 | 100 | 88.5 | 8.0 | 3.5 | 1:8 |
| supernatant after dialysis | 91.1 | 92.7 | 5.8 | 1.5 | 1:8 |
| supernatant after 1st DEAE treatment | 85.2 | 97.4 | 1.9 | 0.7 | 0 |
| supernatant after 2nd DEAE treatment | 83.3 | 97.9 | 1.5 | 0.6 | 0 |
| after acid stabilization | 82.8 | 97.8 | 1.6 | 0.6 | 0 |
| supernatant after 3rd DEAE treatment | 79.7 | 98.6 | 1.1 | 0.3 | 0 |
| supernatant after PEG 1,000 | 77.2 | 99.1 | 0.9 | 0 | 0 |
| after dialysis | 76.4 | 99.1 | 0.9 | 0 | 0 |

Table 1:

The protein content of the solution obtained after dissolution of precipitate II-1,2 was set equal to 100%.

The content of IgA was determined by the Ouchterlony technique.

The distribution of monomers, dimers and polymers was determined by HPLC (LKB, column TSK G 3000 SW 7.5×600 mm).

EXAMPLE 2

49.65 g of Cohn precipitate II-1,2 with a protein content of 26.2% were dissolved in 50 ml of demineralized water, and the solution was dialyzed against running demineralized water for 2 days. 400 ml of demineralized water were added to the solution, which was then centrifuged.

The supernatant was adjusted to a pH of 2.92 by addition of 1 N HCL and, after stirring for 10 minutes, the pH was readjusted to 3.28 by addition of the requisite amount of 1 N NaOH. The protein solution was stored at +4° C. overnight and then adjusted to a pH of 8.3 by further addition of 1 N NaOH in order to achieve optimal precipitation out of labile proteins. The precipitate was removed by centrifugation and discarded.

The same volume of demineralized water was added, and then 20 mg of DEAE-Sephadex A50 per gram of protein were added. The mixture was stirred at +4° C. for one hour. The ion exchanger was removed by filtration, and the pH of the protein solution was adjusted to 7.0. The stirring with 20 mg of DEAE-Sephadex A50 per gram of protein at +4° C. for 1 hour was repeated, and then the ion exchanger was removed by filtration. The immunoglobulin solution was stabilized by addition of glycine (15 g/l) and sodium chloride (7 g/l), and the pH was adjusted to 7.0.

Subsequently, a precipitation was carried out by addition of PEG 600 to a concentration of 15% (w/w). This precipitation was stored at +4° C. overnight, and then the precipitate was removed by centrifugation.

The removal of PEG 600 and the concentration to a protein content of 50.27 mg/ml were carried out as in Example 1.

Yield: 199 ml

Anticomplementary activity: 18.2

|  | % protein | % monomers | % dimers | % polymers | IgA titer |
|---|---|---|---|---|---|
| dissolved Cohn precipitate II-1,2 | 100 | 88.5 | 8.1 | 3.4 | 1:8 |
| supernatant after dialysis | 89.9 | 93.4 | 5.2 | 1.4 | 1:8 |
| after acid stabilization | 89.1 | 93.0 | 5.3 | 1.7 | 1:8 |
| supernatant after 1st DEAE treatment | 82.9 | 97.0 | 2.2 | 0.8 | 0 |
| supernatant after 2nd DEAE treatment | 80.2 | 98.3 | 1.3 | 0.4 | 0 |
| supernatant after PEG 600 | 78.0 | 99.4 | 0.6 | 0 | 0 |
| after dialysis | 76.9 | 99.4 | 0.6 | 0 | 0 |

Table 2:

The protein content of the solution obtained after dissolution of precipitate II-1,2 was set equal to 100%.

The content of IgA was determined by the Ouchterlony technique.

The distribution of monomers, dimers and polymers was determined by HPLC (LKB, column TSK G 3000 7.5×600 mm).

EXAMPLE 3

30 g of Cohn precipitate II-1,2 with a protein content of 28% were stirred with 30 ml of demineralized water at 4° C. The subsequent eugolbulin precipitation was carried out in analogy to Example 1. The supernatant was mixed with 25 mg of DEAE-Sephadex A50/g protein, the pH was corrected to 7.0, the suspension was stirred at 4° C. for 2 hours, and the ion exchanger was removed by filtration through a Buchner funnel.

The filtrate was adjusted to a pH of 2.9 by addition of 1 N HCL. After stirring for 10 minutes, the pH was adjusted to 3.3 by addition of ammonia solution, and the solution was stored at +4° C. overnight.

The pH was raised to 7.5 by addition of ammonia solution, and the solution was heated to 45° C. and maintained at this temperature for 30 minutes. Cooling was followed by removal of the denatured proteins by centrifugation.

The supernatant was mixed once again with 25 mg of DEAE-Sephadex A50/g protein, the pH was adjusted back to 7.0, the solution was stirred at 4° C. for 2 hours, and the ion exchanger was removed by filtration.

A further precipitation out of high molecular weight impurities and oligomeric forms of IgG was carried out by addition of PEG 1,000 as a 50% strength aqueous solution to a concentration of 10% (w/w) and storage at +4° C. overnight.

After the centrifugation, the pure IgG solution was stabilized by addition of glycine (15 g/l) and NaCL (7 g/l). The PEG 1,000 was removed, and the IgG solution was concentrated to 50.26 mg of protein per ml, by ultraand diafiltration as in Example 1.

Yield: 124 ml

Anticomplementary activity: 19.8

|  | % protein | % monomers | % dimers | % polymers | IgA titer |
|---|---|---|---|---|---|
| dissolved precipitate II-1,2 | 100 | 88.3 | 8.3 | 3.4 | 1:8 |
| supernatant after | 75.4 | 99.6 | 0.4 | 0 | 0 |

-continued

|  | % protein | % monomers | % dimers | % polymers | IgA titer |
|---|---|---|---|---|---|
| PEG 1,000 after dialysis | 74.2 | 99.5 | 0.5 | 0 | 0 |

Table 3:

The protein content of the solution obtained after dissolution of precipitate II-1,2 was set equal to 100%.

The content of IgA was determined by the Ouchterlony technique. The distribution of monomers, dimers and polymers was determined by HPLC (LBK, column TSK G 3000 7.5×600 mm).

EXAMPLE 4

Production of a freeze-dried preparation.

50.1 g of Cohn precipitate II-1,2 with a protein content of 29.6% were dissolved in 50 ml of demineralized water, and the solution was dialyzed against running tapwater for 2 days and against demineralized water for one day. 400 ml of demineralized water were added, and then the very cloudy solution was adjusted with NaCL to a concentration of 1 mmol/l, the pH was corrected to 7.0, and the mixture was centrifuged. The supernatant was mixed with 50 mg of DEAE-Sephadex A50 per gram of protein, and the mixture was stirred at +4° C. for 2 hours. The ion exchanger was removed by filtration through a Buchner funnel.

The immunoglobulin solution was adjusted to a content of 15 g/l glycine and 7 g/l NaCL. PEG 1,000 (as a 50% strength aqueous solution) was added to a concentration of 10% (w/w) to precipitate out labile and readily aggregated proteins, the precipitation being stored at +4° C. overnight. The precipitate was then removed by centrifugation.

The protein concentration was increased to 50.03 g/l, and the PEG 1,000 was removed, by ultra- and diafiltration. The immunoglobulin G solution was filtered to clarify and sterilize and then dispensed into containers and freeze-dried.

Yield: 222 ml

Anticomplementary activity: 20.9

|  | % protein | % monomers | % dimers | % polymers | IgA titer |
|---|---|---|---|---|---|
| dissolved precipitate II-1,2 | 100 | 87.4 | 8.5 | 4.1 | 1:16 |
| supernatant after dialysis | 90.2 | 92.7 | 5.7 | 1.6 | 1:8 |
| supernatant after DEAE treatment | 83.0 | 96.6 | 2.5 | 0.9 | 0 |
| supernatant after PEG 1,000 | 78.4 | 98.8 | 1.2 | 0 | 0 |
| after dialysis | 74.9 | 98.7 | 1.3 | 0 | 0 |

Table 4:

The protein content of the solution obtained after dissolution of precipitate II-1,2 was set equal to 100%.

The content of IgA was determined by the Ouchterlony technique.

The distribution of monomers, dimers and polymers was determined by HPLC (LBK, column TSK G 3000 7.5×600 mm).

What we claim is:

1. A process for the preparation of a chemically unmodified, functionally and structurally intact immunoglobulin which has not been enzymatically treated, has no side effects, contains all IgG subclasses, is essentially free of IgA, is stable on storage in liquid form and can be administered intravenously, and which has a monomer content of above 97% and a content of trimers and higher polymers of below 1%, by subjecting a starting fraction having an IgG content between 30 and 100% to purification and concentration by the steps dialysis, adsorption and precipitation, which comprises (a) dialysis of an aqueous solution of the starting fraction to remove low molecular weight constitutents, lowering the ionic strength at a pH of 6.0–9.0 by diluting the mixture with demineralized water and setting up a sodium chloride concentration of 1 mmol/l in order to remove euglobulins, removal of impurities from the supernatant from the euglobulin precipitation by adsorption once or twice on an anion exchanger in an amount of 5–50 mg/g protein at a pH of 6.0 to 9.0, (b) stabilization of the solution by acid treatment at pH 2.5–4.2, heating at 40–60° C. and pH 3.0–8.0 for 15 to 20 minutes, returning the pH to 7.0–9.0, and removal of the insoluble fractions by centrifugation, (c) removal of IgA and other impurities which are still present by treatment once or twice with an anion exchanger in an amount of 5–50 mg/g protein at pH 6.0–9.0, (d) precipitation of labile and aggregated IgG molecules by addition of polyethylene glycol having a mean molecular weight of 200–1,000 to a final concentration of 10–25% (w/w) and removal thereof by centrifugation, removal of the precipitant, by dialysis or ultrafiltration, adjustment of the solution to the desired protein concentration, and sterilization thereof by filtration.

2. The process as claimed in claim 1, wherein the adsorption in stage (a) is carried out with 10–30 mg of anion exchanger per g of protein at pH 6.5 to 7.5.

3. The process as claimed in claim 1, wherein the acid treatment in stage (b) is carried out in two steps by a pH of 2.9 to 3.1 being adjusted by acidificaiton at 4' C. for 5–10 min., and then the solution being readjusted to a pH of 3.3 to 3.5 and stored for 12 to 24 hours.

4. The process as claimed in claim 1, wherein the heat treatment in stage (b) is carried out at pH 3.0 to 8.0 and at 45 to 55° C. for 30 to 60 min.

5. The process as claimedin claim 1, wherein the treatment with an ion exchanger in stage (c) is carried out at pH 7.0 to 7.5 in an amount of 10–30 mg of ion exchanger per gram of protein.

6. The process as claimed in claim 1, wherein the precipitation in state (d) is carried out with a PEG of a means molecular weight of 600–1,000 to a final concentration of 10–15% (w/w) at pH 6.5–7.5.

7. The process as claimed in claim 1, wherein the low molecular weight PEG used as precipitant is removed by ultrafiltration an the desired protein concentration is simultaneously adjusted by diafiltration.

8. The process as claimed in claim 1, wherein the euglobulin precipitation in stage (a) is carried out at a pH of 6.5 to 7.5.

* * * * *